United States Patent
Carroll

(10) Patent No.: US 6,761,715 B2
(45) Date of Patent: Jul. 13, 2004

(54) METHOD AND DEVICE FOR NEUROCRYO ANALGESIA AND ANESTHESIA

(76) Inventor: Ronald J. Carroll, 255 Western Promenade, Portland, ME (US) 04102

( * ) Notice: Subject to any disclaimer, the term of this patent is extended or adjusted under 35 U.S.C. 154(b) by 135 days.

(21) Appl. No.: 10/071,574

(22) Filed: Feb. 5, 2002

(65) Prior Publication Data

US 2002/0161360 A1 Oct. 31, 2002

Related U.S. Application Data

(60) Provisional application No. 60/286,636, filed on Apr. 26, 2001.

(51) Int. Cl.$^7$ .............................................. A61B 18/18
(52) U.S. Cl. ........................................ 606/21; 128/898
(58) Field of Search ...................... 606/20–26; 128/898

(56) References Cited

U.S. PATENT DOCUMENTS

| | | | |
|---|---|---|---|
| 3,901,241 A | 8/1975 | Allen, Jr. ................. | 128/303.1 |
| 4,202,336 A | 5/1980 | van Gerven ............. | 128/303.1 |
| 4,306,561 A | 12/1981 | de Medinaceli ....... | 128/303.13 |

(List continued on next page.)

FOREIGN PATENT DOCUMENTS

EP          0043447 A2    1/1982    ........... A61B/17/36

OTHER PUBLICATIONS

P. J. D. Evans, Cryoanalgesia, The application of low temperatures to nerves to produce anesthesia or analgesia, Anesthesia, 1981, vol. 36, pp. 1003–1013.

Francis Robiscsek, MD, et al, Biological thersholds of cold–induced phrenic nerve injury, The Journal of Thoracic and Cardiovascular Surgery, Jan. 1990, p. 167–170, vol. 99 No. 1.

Linqui Zhou, et al., Mechanism research of cryoanalgesia, Neurological Research, Aug. 1995, p. 307–311, vol. 17, Forefront Publishing Group.

A. Vania Apkarian, et al., A cryogenic device for reversibly blocking transmission through small regions of the spinal cord white matter, Journal of Neuroscience Methods, Feb. 1989, p. 93–106, 29, Elsevier Science Publishers B.V. (Biomedical Division), Syracuse, NY.

*Primary Examiner*—Michael Peffley
*Assistant Examiner*—Peter J Vrettakos
(74) *Attorney, Agent, or Firm*—Pierce Atwood

(57) ABSTRACT

A catheter system and method for selectively cooling or freezing target neuronal tissue to induce lesions along the neuroaxis and produce cryoanalgesia by impairing nerve conduction of the targeted neuronal tissue. The system includes a catheter that has cryogenic capability for variable cooling or freezing of neuronal tissue. The catheter also includes temperature sensing and electrodiagnostic capabilities. A pressurized fluid source is included for inflating a portion of the catheter body. The system includes electrodiagnostic equipment for stimulating and monitoring sensory evoked potentials in the patient. The method involves placement of the catheter tip in the subarachnoid space of the spinal canal and location of the tip on the neuronal target using imaging and electrodiagnostic techniques.

18 Claims, 8 Drawing Sheets

U.S. PATENT DOCUMENTS

| | | | |
|---|---|---|---|
| 4,646,735 A | | 3/1987 | Seney ..................... 128/303.1 |
| 4,802,475 A | | 2/1989 | Weshahy ................. 128/303.1 |
| 4,904,237 A | * | 2/1990 | Janese .......................... 604/28 |
| 4,936,306 A | | 6/1990 | Doty ......................... 128/642 |
| 5,081,990 A | | 1/1992 | Deletis ...................... 128/642 |
| 5,147,355 A | | 9/1992 | Friedman et al. ............. 606/23 |
| 5,281,213 A | | 1/1994 | Milder et al. ................. 606/15 |
| 5,281,215 A | | 1/1994 | Milder ........................ 606/20 |
| 5,314,423 A | | 5/1994 | Seney ......................... 606/20 |
| 5,336,176 A | * | 8/1994 | Yoon .......................... 604/506 |
| 5,417,686 A | | 5/1995 | Peterson et al. ............. 606/25 |
| 5,423,770 A | * | 6/1995 | Yoon .......................... 604/506 |
| 5,423,807 A | | 6/1995 | Milder ........................ 606/20 |
| 5,591,162 A | * | 1/1997 | Fletcher et al. ............... 606/25 |
| 5,672,172 A | | 9/1997 | Zupkas ........................ 606/20 |
| 5,693,077 A | | 12/1997 | Friedman .................... 607/96 |
| 5,741,248 A | | 4/1998 | Stern et al. ................... 606/21 |
| 5,957,963 A | | 9/1999 | Dobak, III .................. 607/104 |
| 6,051,019 A | | 4/2000 | Dobak, III .................. 607/104 |
| 6,106,517 A | | 8/2000 | Zupkas ........................ 606/20 |
| 6,190,370 B1 | * | 2/2001 | Tsui ........................... 604/508 |
| 6,217,552 B1 | * | 4/2001 | Barbut et al. ............... 604/113 |
| 6,254,599 B1 | | 7/2001 | Lesh et al. ..................... 606/41 |
| 6,272,370 B1 | * | 8/2001 | Gillies et al. ............... 600/411 |
| 6,364,899 B1 | * | 4/2002 | Dobak, III .................. 607/113 |
| 6,379,331 B2 | * | 4/2002 | Barbut et al. ............... 604/113 |
| 6,551,349 B2 | * | 4/2003 | Lasheras et al. ............ 607/105 |
| 2003/0014016 A1 | * | 1/2003 | Purdy ......................... 604/174 |
| 2003/0130651 A1 | * | 7/2003 | Lennox ....................... 606/21 |

* cited by examiner

METHOD AND DEVICE FOR NEUROCRYO ANALGESIA AND ANESTHESIA

CROSS REFERENCES TO RELATED APPLICATIONS

This application claims the benefit of U. S. Provisional Application Ser. No. 60/286,636, filed Apr. 26, 2001.

BACKGROUND OF THE INVENTION

This invention relates generally to cryoanalgesia and more particularly to devices and procedures for applying cryoanalgesia to the neuroaxis.

Management of acute and chronic pain has been a concern for as long as medicine has been practiced. Many methods of inducing analgesia and anesthesia have been developed. The use of chemical substances is perhaps the most common approach to pain relief. This approach requires suitable substances that are effective, safe to humans, and do not cause complications or abnormal reactions. Despite the great advances that have been made in the field of anesthesiology, and in the field of pain relief in general, there are still some drawbacks to chemical-based approaches. For instance, the anesthetics generally available today must be administered in carefully graduated doses to assure the patient's well being, require extended periods of fasting prior to treatment, and are often accompanied by undesirable after effects such as nausea.

An alternate approach that avoids these drawbacks is cryoanalgesia, which is a safe and effective approach to providing prolonged pain relief without the complications or undesirable after effects often experienced with chemical-based approaches. As used herein, the term "cryoanalgesia" refers to cooling or freezing of neuronal tissue (nerves, synapses, ganglia, etc.) to produce analgesia or anesthesia. Attempts to use tissue cooling or freezing to control pain have been known since antiquity. Surgery using cold packs and the painless amputation of frozen limbs during wartime are part of military medical history. In the nineteenth century, attempts were made to use tissue cooling to treat a wide range of maladies. Twentieth century studies have shown that the cooling or freezing of neuronal tissue reduces or eliminates pain by interrupting nerve conduction. Cooling neuronal tissue to temperatures in the range of zero to −4 degrees centigrade, and sometimes below, causes analgesia lasting from days to weeks. Neuronal tissues cease functioning when sufficiently cooled, but before becoming frozen. Freezing neuronal tissue (i.e., reducing tissue temperature to −4 to −20 degrees centigrade or below) causes profound long lasting, usually permanent but sometimes reversible, anesthesia of the innervated part. There may well be different outcomes of cooling and freezing, depending on whether the treatment is applied to neuronal axons or neuronal cell bodies (containing the nucleus).

A number of devices for the controlled cooling and/or freezing of small volumes of tissue are available. Rigid cryoprobes exist for percutaneous use or in open invasive surgical procedures. For example, cryoprobes are used for freezing a range of lesions from prostate tissue to metastatic cancers in liver. Neuronal tissue has been frozen with such devices for the relief of pain. Such devices have been in use for more than 20 years.

Cryocatheters or cryogenic catheters are of more recent evolution and have been used by way of the blood vascular route to destroy, by freezing, conducting tissues in the heart for the correction of cardiac arrhythmia. Such cyrocatheters are not designed for cryoanalgesia.

In both these types of systems, coolant gases under pressure are delivered to the tip of the instrument (i.e., the probe or catheter) where expansion of the gas is used to create temperatures as low as −60 degrees centigrade or below which cools or freezes the tissues in the local area around the tip. The size and configuration of the lesion created will depend in large part on a configuration of the tip. The effect obtained will depend upon the rate of cooling, degree of cooling, and the duration of cooling, as well as specifics of the tissue and environment.

While conventional cryoprobes used to treat neuronal tissue can produce excellent results, they generally can be used only for certain percutaneous procedures in which the target neuronal tissue is readily accessible by the rigid probes or for open surgical procedures. These restrictions greatly limit the opportunities for using cryoanalgesia. Accordingly, it would be desirable to have a device and method that would allow a more extensive use of cryoanalgesia.

SUMMARY OF THE INVENTION

The above-mentioned need is met by the present invention, which provides a catheter including a catheter body having a proximate end and a distal end, means for holding the distal end adjacent to a neuroaxis structure target, and means for internally delivering a coolant fluid to the distal end of the catheter body. In one possible embodiment, the catheter body is a tube having first and second chambers formed therein. The means for holding includes an expandable portion formed in the tube and a pressurized fluid source connected to the first chamber for inflating the expandable portion, and the means for internally delivering a coolant fluid includes a delivery tube disposed in the second chamber and a source of coolant fluid connected to the delivery tube. A temperature detector can be disposed on an external surface of the catheter body.

The present invention can also include an electrically conductive tip member formed on an external surface of the catheter body, an external electrode for application to a patient's body, and a monitoring/stimulating device electrically connected to the tip member and to the external electrode. The device is capable of delivering an electrical stimulus to the external electrode and measuring sensory evoked potentials in response to input from the tip member.

In use, the distal end of the catheter is inserted into the subarachnoid space of a patient and positioned adjacent to a neuronal tissue target. A portion of the catheter is inflated to hold the distal end in position on the target neuronal tissue. The external electrode is placed on a dermatome on the patient that corresponds to the neuronal tissue target. The monitoring/stimulating device can then be used to deliver an electrical stimulus to the dermatome (which will be transmitted centrally over sensory afferent nerve fibers) and measure resultant sensory evoked potentials detected at the tip member. Measurement of sensory evoked potentials can be used to verify that the distal end is properly positioned relative to the neuronal tissue target, since coolant fluid is delivered into the catheter so as to effect cooling or freezing of the neuronal tissue target and stop neuronal nerve conduction.

The present invention and its advantages over the prior art will become apparent upon reading the following detailed description and the appended claims with reference to the accompanying drawings.

DESCRIPTION OF THE DRAWINGS

The subject matter that is regarded as the invention is particularly pointed out and distinctly claimed in the concluding part of the specification. The invention, however, may be best understood by reference to the following description taken in conjunction with the accompanying drawing figures in which:

DETAILED DESCRIPTION OF THE INVENTION

The highly structured neuroaxis (the spinal cord and spinal nerves) lends itself to cryoanalgesia techniques to produce analgesia or anesthesia of body parts innervated by the target nerve tissue. This is accomplished by selective cooling or freezing of the target neuronal tissue using a neurocryocatheter system to induce lesions along the neuroaxis. The neuro-cryocatheter system is used to diagnose, monitor and interfere with nerve conduction along the spinal cord axis by invading the cerebrospinal fluid canal (subarachnoid space) by way of percutaneous puncture. The cooling or freezing of neuronal tissue produces analgesia or anesthesia (i.e., "cryoanalgesia") by impairing nerve conduction of the targeted neuronal tissue. The neuro-cryocatheter system of the present invention may be used not only on human patients but on other animals, particularly vertebrates, as well.

Figure 6:
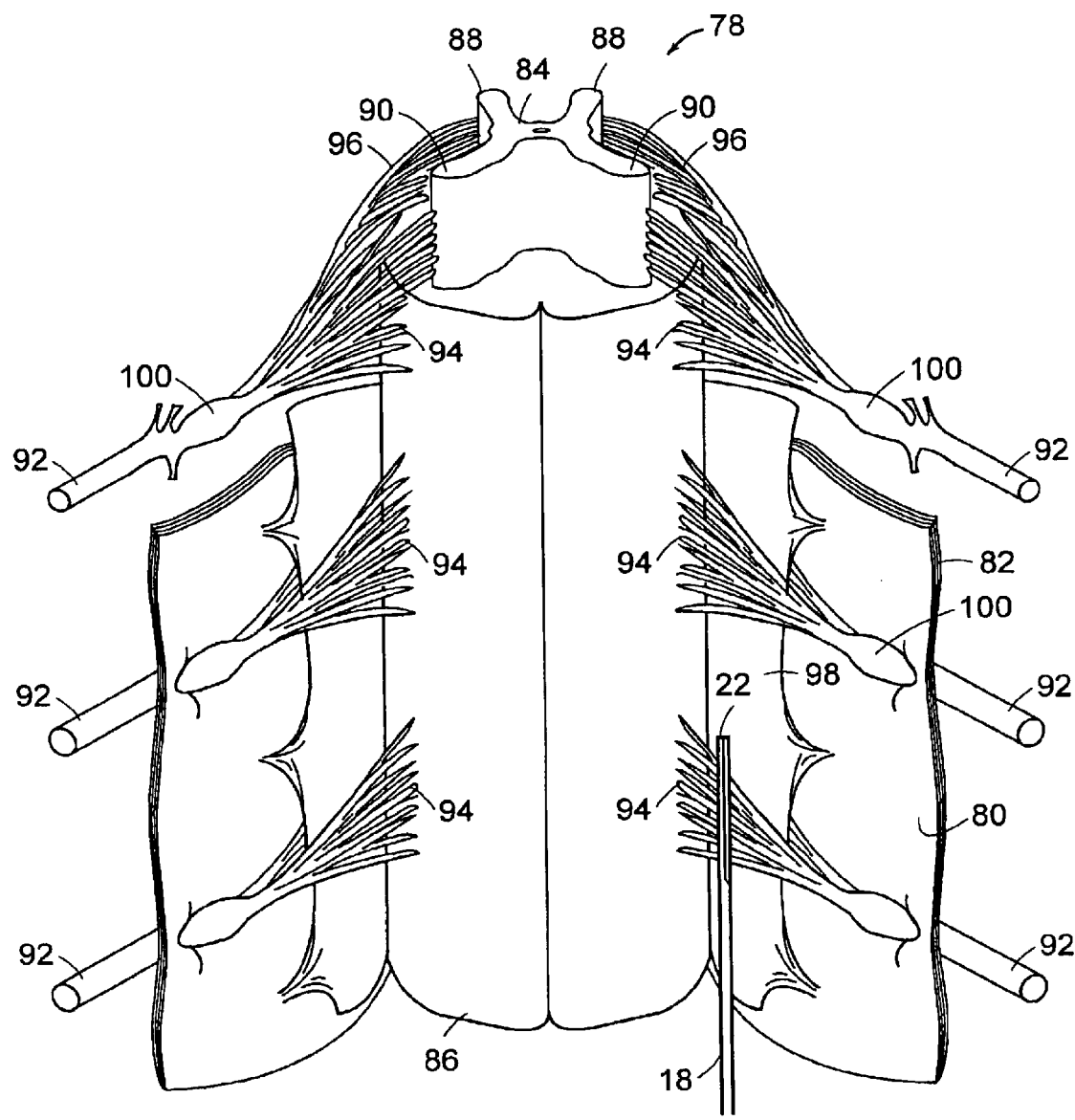
FIG. 6 is a dorsal view, in partial cutaway, of a portion of a spinal cord.
Figure 7:
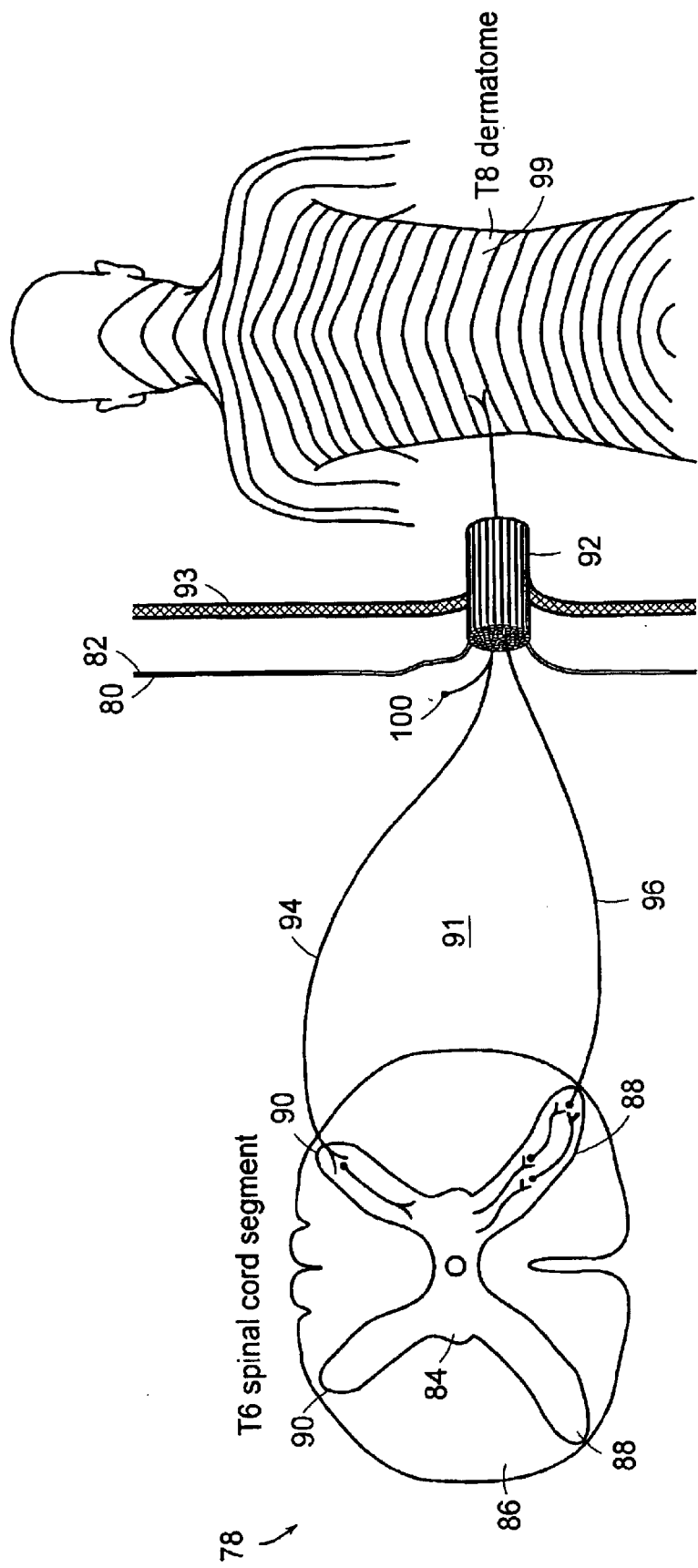
FIG. 7 is a composite schematic diagram showing the relationship between a spinal cord segment and its corresponding dermatome.
Figure 9A:
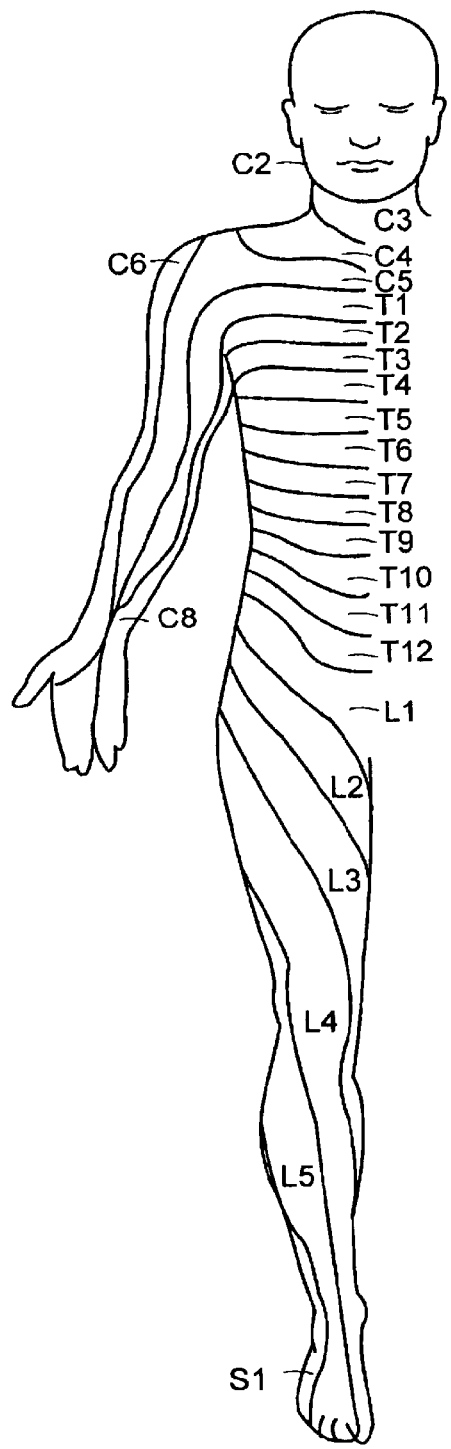
FIG. 9A is a partial dorsal view of a human body showing its dermatomes.
Figure 9B:
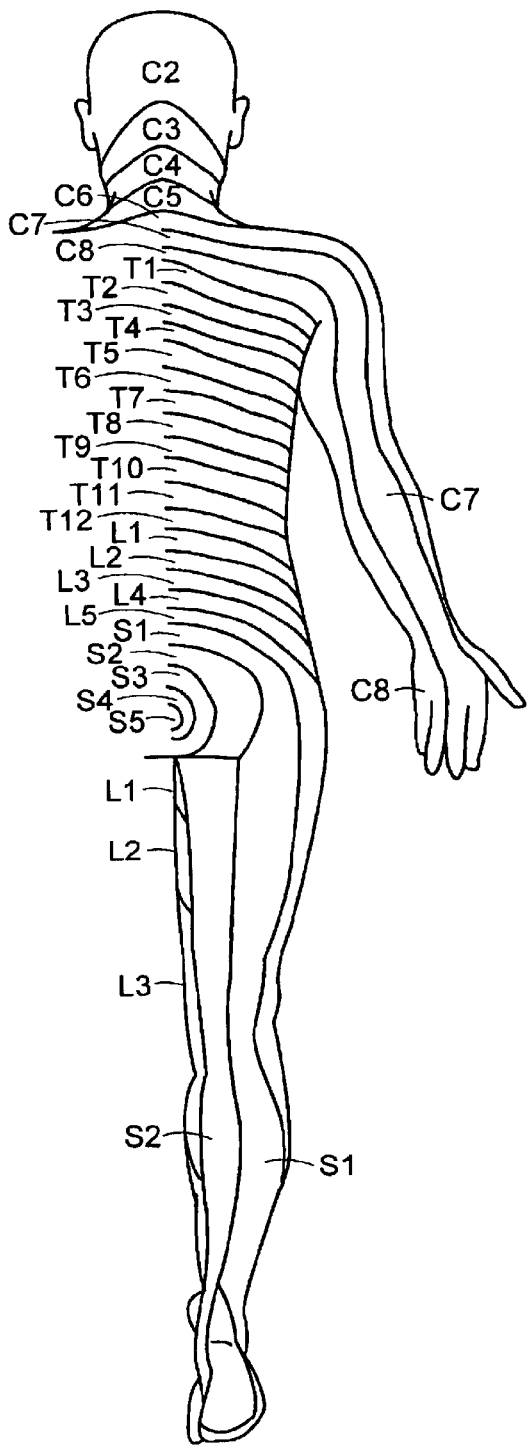
FIG. 9B is a partial ventral view of a human body showing its dermatomes.

Generally referring to FIGS. 6 and 7 (which are discussed in more detail below), a basic discussion of neuroaxis anatomy is provided to facilitate understanding of the present invention. The human spinal cord is functionally segmented along its length, giving rise to 30 pairs of spinal nerves. The skin is likewise segmented into dermatomes (see FIGS. 9A and 9B). A dermatome is an area of skin contributing sensory afferent nerve fibers to a corresponding spinal cord segment. There is substantial (85%) correspondence between the enervation of skin dermatomes and cord segments. The skin (and deeper structures) and the spinal cord are connected by neurons (primary sensory or afferent neurons) which have sensory receptor endings, including pain receptors in the skin (and deeper structures). The bodies of the primary sensory nerves are found in the dorsal root ganglion, just inside the dural lining of the spinal canal. When sensory nerves are stimulated, a nerve impulse travels over the primary neuron, entering the spinal cord at the corresponding segment by way of the dorsal root nerve filaments. The neuron that transmits the impulse connects the dermatome to its corresponding spinal cord segment. These filaments are longitudinally arranged along the cord as shown in FIG. 6. In the aggregate, these filaments combined are called a dorsal root. The axons of sensory neurons terminate on secondary nerve cell bodies (gray matter) found in the dorsal horn of the spinal cord itself.

The ventral horn of the spinal cord is composed of neuronal bodies of nerves providing enervation of muscles. The axons of motor neurons leave the spinal cord becoming the ventral nerve root filaments. The ventral nerve root filaments and the dorsal nerve filaments are separated by the denticulate ligaments. Just lateral to the dorsal nerve ganglion, the ventral nerve filaments join to form a mixed nerve that travels to the periphery of the body. Mixed nerves therefore carry sensory nerve impulses into the cord and motor nerve impulses away from the cord. Impairing nerve conduction in a mixed nerve impairs both sensory and motor function. Impairing ventral nerve filaments alone impairs only motor function. Impairing dorsal nerve filaments alone impairs only sensory function.

Neurons are composed of cell bodies (nerve bodies) and appendages (axons and dendrites). Cell bodies contain the cell nucleus and other structures essential for the life of the neuron. Axons are extensions of the neuronal cell body of variable length (sometimes a meter long) that conduct electrochemical nerve impulses from the skin (and deeper structures) sensory receptors to the spinal cord where, after entering the cord they synapse on secondary nerve bodies found in the dorsal horn. Axons in the aggregate form nerve filaments. The nerve bodies of the primary sensory neurons are found in the dorsal ganglion. The dorsal ganglion is a collection of nerve bodies found just inside the dura, lateral to the spinal cord and proximal to the formation of the mixed spinal nerve. It should be stressed that the dorsal nerve filaments are formed of aggregates of the axons of the sensory nerves coming from specific dermatomes (and related deeper structures) and going to specific segments of the spinal cord.

Individual axons are within a fine tube of connective tissue called the endoneureon. If axons are destroyed, they will regenerate over time (weeks to months) and resume functioning, as long as the endoneureon tube remains intact, and the nerve cell body remains intact. Freezing axons destroys them, but leaves the endoneureon intact. Freezing nerve cell bodies irreversibly destroys the nerve by killing the cell body. Axons cannot regenerate if the cell body is destroyed. Cooling cell bodies or axons to about 0–20 degrees centigrade causes a reversible cessation of nerve transmission. (See: A. Vania Apkarian et al., *A Cryogenic Device for Reversibly Blocking Transmission Through Small Regions of the Spinal Cord White Matter*, Journal of Neuroscience Methods, 29 (1989) pp. 93–106, and Linqiu Zhou et al., *Mechanism Research of Cryoanalgesia*, Neurological Research, Vol. 17, August 1995, pp. 307–311.) This interruption in function may last for minutes to hours.

In one embodiment, the present invention provides prolonged relief of pain through selection of appropriate neuronal targets and freezing those targets to temperatures that result in prolonged impairment of neuronal function. Dorsal root nerve filaments are appropriate targets for such relief of chronic pain. Candidate dermatomes and corresponding dorsal nerve root filaments are determined by the clinical pain pattern.

Referring to the drawings wherein identical reference numerals denote the same elements throughout the various views, FIGS. 1–4 show a neuro-cryocatheter system for the cooling or freezing of neuroaxis structure targets. The system includes an introducer 10 shown in FIG. 1. The introducer 10 comprises a stylet 12 encased by a sheath 14. The stylet 12 has a sharp, pointed tip 16 capable of penetrating soft tissue overlying the spinal canal. Once the introducer 10 has been inserted into the desired location, the stylet 12 is removed and the sheath 14 is left in place to function as a cannula. Preferably, the introducer 10 has an outer diameter of about 1.5 millimeters or less and a length of typically 4–5 inches.

Figure 1:
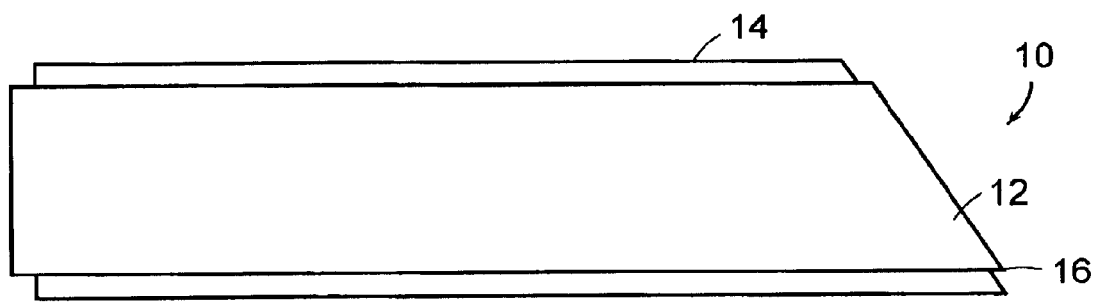
FIG. 1 is a longitudinal cross-sectional view of an introducer from a neuro-cryocatheter system of the present invention.
Figure 2:
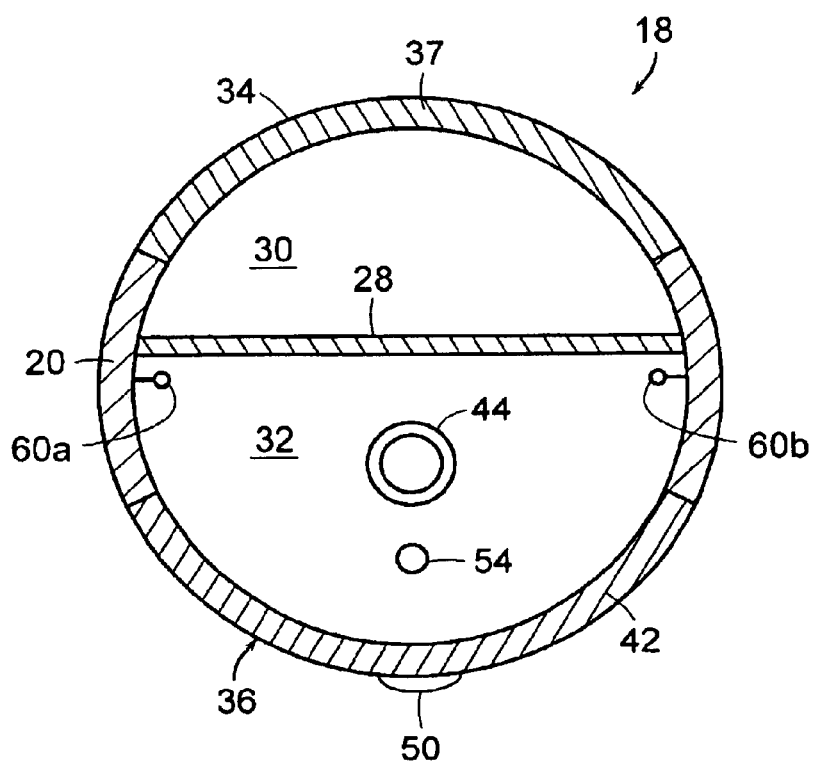
FIG. 2 is a longitudinal cross-sectional view of cryocatheter from a neuro-cryocatheter system of the present invention.
Figure 3:
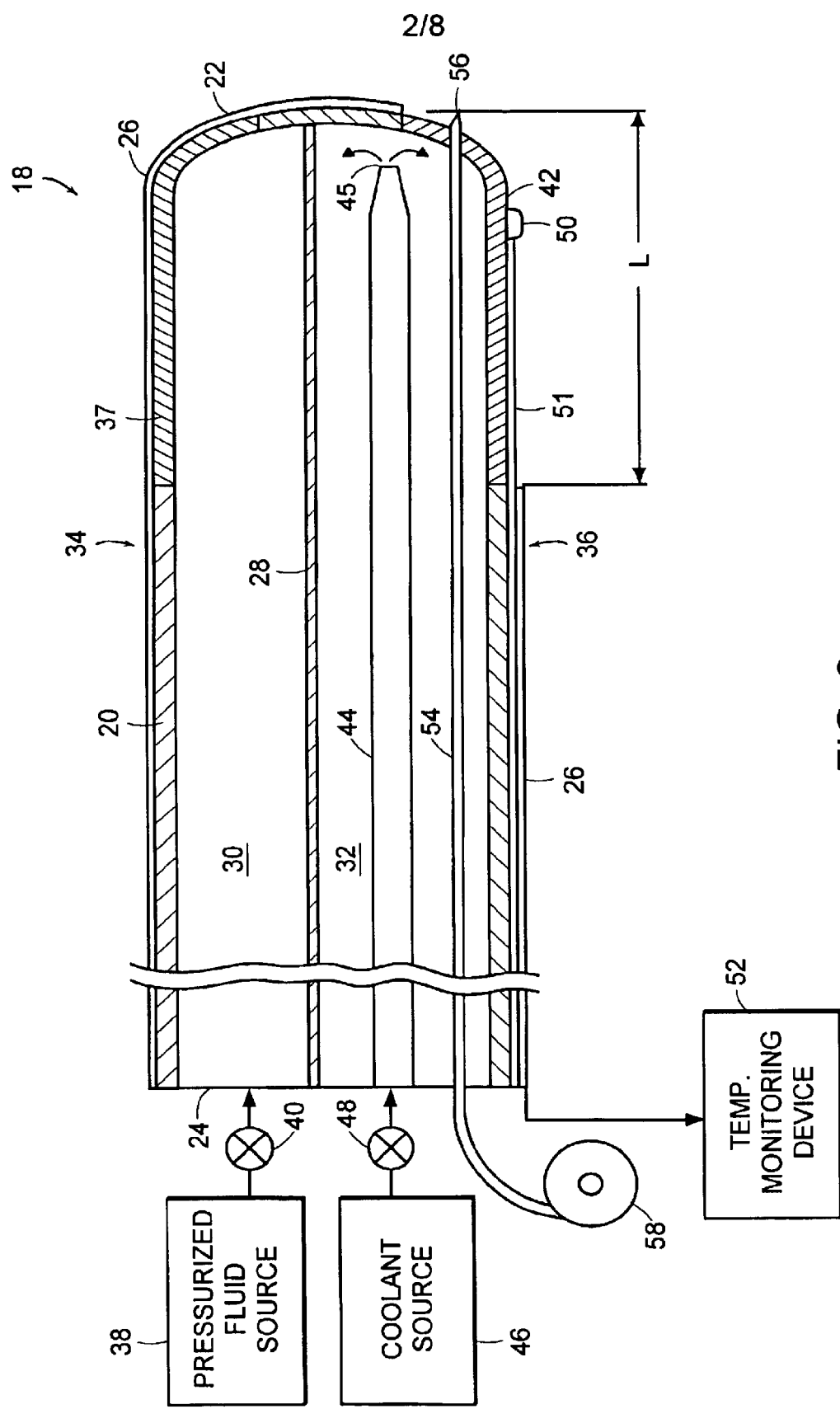
FIG. 3 is an axial cross-sectional view of the cryocatheter of FIG. 2.
Figure 4:
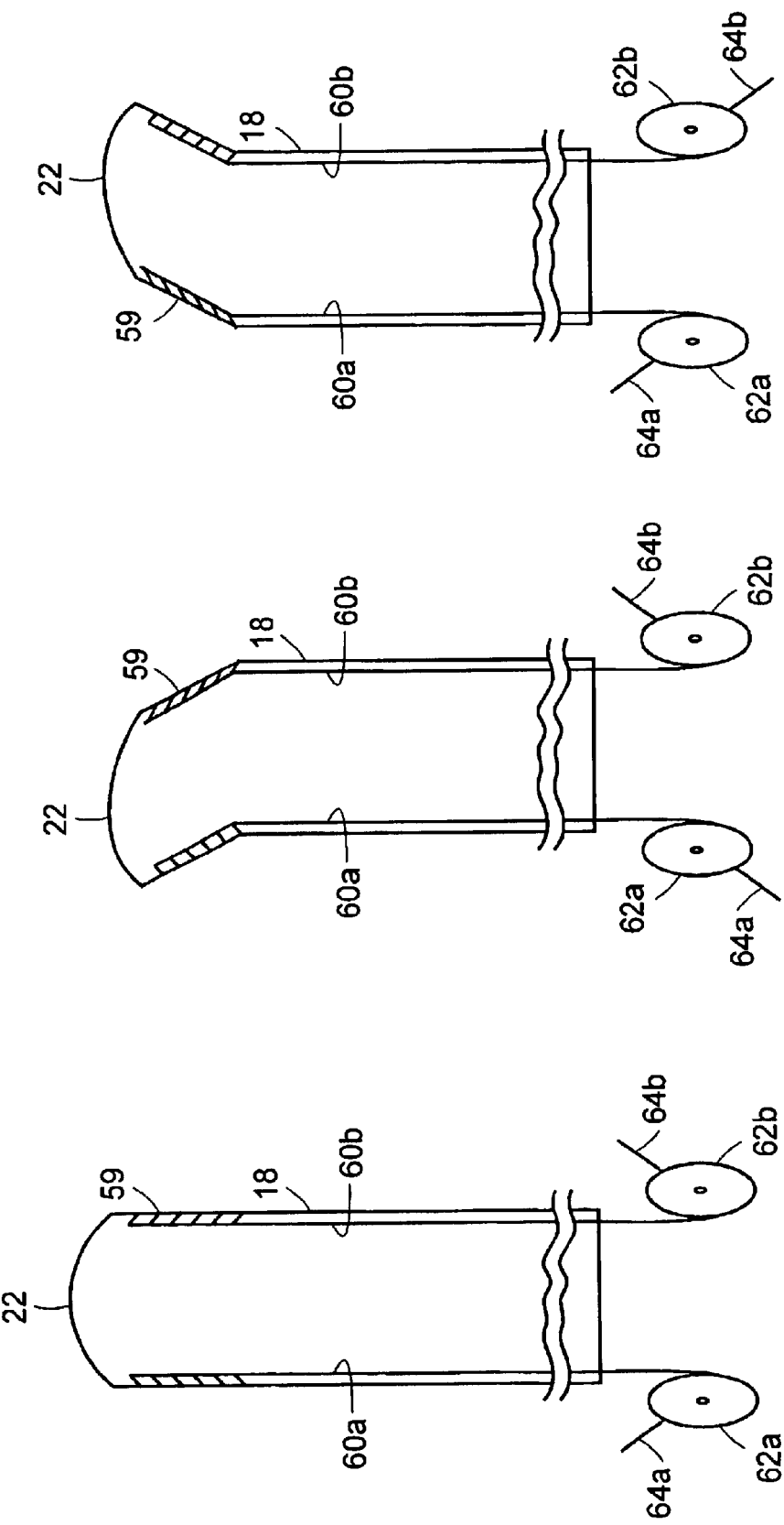
FIGS. 4A–4C are schematic views of the cryocatheter showing a means for angling a distal tip portion of the cryocatheter.

FIGS. 2 and 3 show a cryocatheter 18 for insertion into the sheath 14 after the sheath 14 has been positioned in the patient's body. The cryocatheter 18 has a diameter small enough to fit into the sheath 14 and has a length of about 6–36 inches. The cryocatheter 18 includes a catheter body 20 in the form of a hollow outer tube having a distal end 22 that is insertable through the positioned sheath 14 and a proximate end 24 that remains outside of the body. Although the outer tube 20 is shown as having a circular cross-section, it should be noted that the present invention is not so limited and the cryocatheter 18 can have a variety of configurations. The catheter body or outer tube 20 is made of a non-rigid material and is thermally insulated with a coating 26 of insulating material. A septum 28 is formed inside the outer tube 20 and extends the length thereof to divide the tube interior into first and second chambers 30 and 32. When the cryocatheter 18 is in use, the section thereof encompassing the first chamber 30 will correspond to the dorsal or posterior side of the cryocatheter 18, and the section encompassing the second chamber 32 will correspond to the ventral or anterior side of the cryocatheter 18. The cryocatheter 18 thus has a dorsal side 34 and a ventral side 36. The cryocatheter 18 is preferably made, at least in part, of a material suitable for radiologic imaging.

The outer tube 20 has an expandable portion 37 formed at the distal end 22, on the dorsal side 34 so as to be in fluid communication with the first chamber 30. The expandable portion 37 comprises a section of expandable material formed in the outer tube 20. The remainder of the outer tube 20 is made of a material that is not expandable, or at least not as expandable as the material of the expandable portion 37. A pressurized fluid source 38 is connected with the first chamber 30 via a valve 40. The valve 40 can be operated to allow pressurized fluid from the source 38 to flow into the first chamber 30 and inflate the expandable portion 37 so that the distal end 22 is larger in cross-section than the rest of the outer tube 20. The valve 40 can also be operated to allow pressurized fluid to escape from the first chamber 30 so that the expandable portion 37 deflates.

The outer tube 20 includes a tip member 42 formed on the external surface of the ventral side 36, at the distal end 22. The tip member 42 is made of an electrically conducting material and is not thermally insulated. That is, the coating 26 does not cover the tip member 42. A coolant delivery tube 44 is disposed in the second chamber 32, preferably coaxial therewith. One or more expansion openings 45 are formed in the distal end of the coolant delivery tube 44, which is located adjacent to the distal end 22 of the outer tube 20 and the tip member 42. The proximate end of the coolant delivery tube 44 is connected to a source of pressurized coolant fluid (gas or liquid) 46 via another valve 48. The pressurized coolant fluid flows, under control of the valve 48, down the coolant delivery tube 44 and exits through the expansion opening(s) 45 into the second chamber 32. The coolant fluid expands and cools as it is discharged through the expansion opening(s) 45. Thus, the temperature of the non-insulated tip member 42 will be greatly reduced in a controllable manner such that neuronal tissue in contact with or adjacent to the tip member 42 will be cooled or frozen. The spent coolant fluid flows back through the second chamber 32 and exits through the proximate end 24 in a manner known in the art.

It should be noted that the present invention is not limited to a catheter body comprising a single tube separated into two chambers by a septum. Another possible configuration includes a catheter body formed from two catheters joined together lengthwise. One of the catheters would be an expandable catheter corresponding to the dorsal side 34; the other catheter would be a cryocatheter corresponding to the ventral side 36.

The geometry of the tip member 42 will be determined based on the location and nature of the anatomic target site to be treated, which are discussed in more detail below. Generally, the tip member 42 has a substantially semi-cylindrical shape, as shown in FIG. 2. The length, L, of the tip member 42 (FIG. 3) will be dependent on the anatomic target site to be treated. For example, given the arrangement of afferent filaments entering the dorsal horn (i.e., filaments may enter over several centimeters of the cord for a single nerve), the tip member length would be approximately equal to this length if the nerve filaments are the target. If the target were a dorsal ganglion, a shorter, smaller diameter tip member 42 would be desirable. If the entire posterior cord were to be treated, a longer tip member would be used. If generalized cooling of a substantial part or segment of the cord itself is desired (as to induce spinal anesthesia), then the tip member 42 would be configured to accommodate that objective.

A temperature detector 50 is located on the external surface of the tip member 42. The temperature detector 50, which can be any suitable device such as a thermocouple, can be used to provide feedback, via electric wire 51 connected to an external temperature monitoring device 52, of the tip member temperature during a treatment procedure so that the flow of coolant fluid can be controlled accordingly to obtain the desired temperature.

The cryocatheter 18 optionally includes a hollow conduit 54 disposed inside the second chamber 32 of the outer tube 20, adjacent to the coolant delivery tube 44. The hollow conduit 54 has a distal needle tip 56 and is movable longitudinally within the outer tube 20 by a rotatable head 58 located outside of the tube 20 and attached to the proximate end of the hollow conduit 54. The needle tip 56 can be extended beyond the distal end 22 (as shown in FIG. 3) or retracted back into the outer tube 20 by turning the rotatable head 58 in the appropriate direction. The head 58 can be calibrated so as to indicate how much the needle tip 56 is extended. With the needle tip 56 extended, the hollow conduit 54 can be used for local injections of pharmaceuticals. The hollow conduit 54 could be used diagnostically to verify the proper location of the distal end 22. That is, once the distal end 22 was believed to be located at the desired target site, a small dose of an analgesic drug could be injected via the hollow conduit 54. If the patient experienced pain relief in the affected part, this would indicate that the distal end 22 and the tip member 42 are properly located. As an alternative embodiment, it is possible to use a catheter tip configured to deliver pharmaceuticals in gel form.

In addition, the cryocatheter 18 optionally includes a means for changing the angle of a distal tip portion 59 of the cryocatheter 18 relative to the rest of the cryocatheter 18.

One possible tip angle changing means is illustrated schematically in FIGS. 4A–4C. In this arrangement, two guide wires 60a and 60b are disposed inside the outer tube 20 on diametrically opposing sides thereof. As seen in FIG. 2, the guide wires 60a and 60b are located adjacent to the opposing sides of the septum 28 so as to provide for lateral adjustment of the tip angle. The distal end of each guide wire 60a and 60b is fixedly attached to the distal tip portion 59 of the outer tube 20. A first rotatable head 62a is located outside of the tube 20 and is attached to the proximal end of the first guide wire 60a, and a second rotatable head 62b is located outside of the tube 20 and is attached to the proximal end of the second guide wire 60b. The first and second rotatable heads 62a and 62b are rotatively mounted to a handle (not shown) and have first and second levers 64a and 64b, respectively, formed thereon. The levers 64a and 64b are positioned such that a user holding the handle can manipulate the levers 64a and 64b independently to turn the corresponding rotatable head 62a and 62b. Turning the first and second heads 62a and 62b in the appropriate direction will pull the corresponding guide wire 60a and 60b relative to the outer tube 20. Because the far end of each guide wire 60a and 60b is fixedly attached to the distal tip portion 59, pulling one of the guide wires 60a and 60b causes the distal tip portion 59 to bend relative to the rest of the outer tube 20. (The catheter structures are all made of a flexible material.) Specifically, pulling the first guide wire 60a causes the distal tip portion 59 to bend to the left as shown in FIG. 4B, while pulling the second guide wire 60b causes the distal tip portion 59 to bend to the right as shown in FIG. 4C. The rotatable heads 62a and 62b are calibrated so that the tip angle can be accurately controlled. Adjusting the tip angle permits the tip member 42 to be positioned adjacent to a wider range of neuroaxis targets.

As mentioned above, the tip member 42 is electrically conducting and can thus function as an electrode for electrodiagnostic purposes. This is accomplished using sensory evoked potentials, which are central nervous system electrical potentials that have traditionally been measured from scalp electrodes after a stimulus is applied to a peripheral nerve or a dermatome. (A dermatome is an area of skin contributing sensory afferent nerve fibers to a spinal nerve (s); there is an anatomic correspondence between a given dermatome and a given dorsal nerve root.) Because evoked potentials as currently measured are remote from the stimulus and are the result of multiple neuronal interactions, they are small in amplitude and difficult to measure above background noise using conventional equipment.

Figure 5:
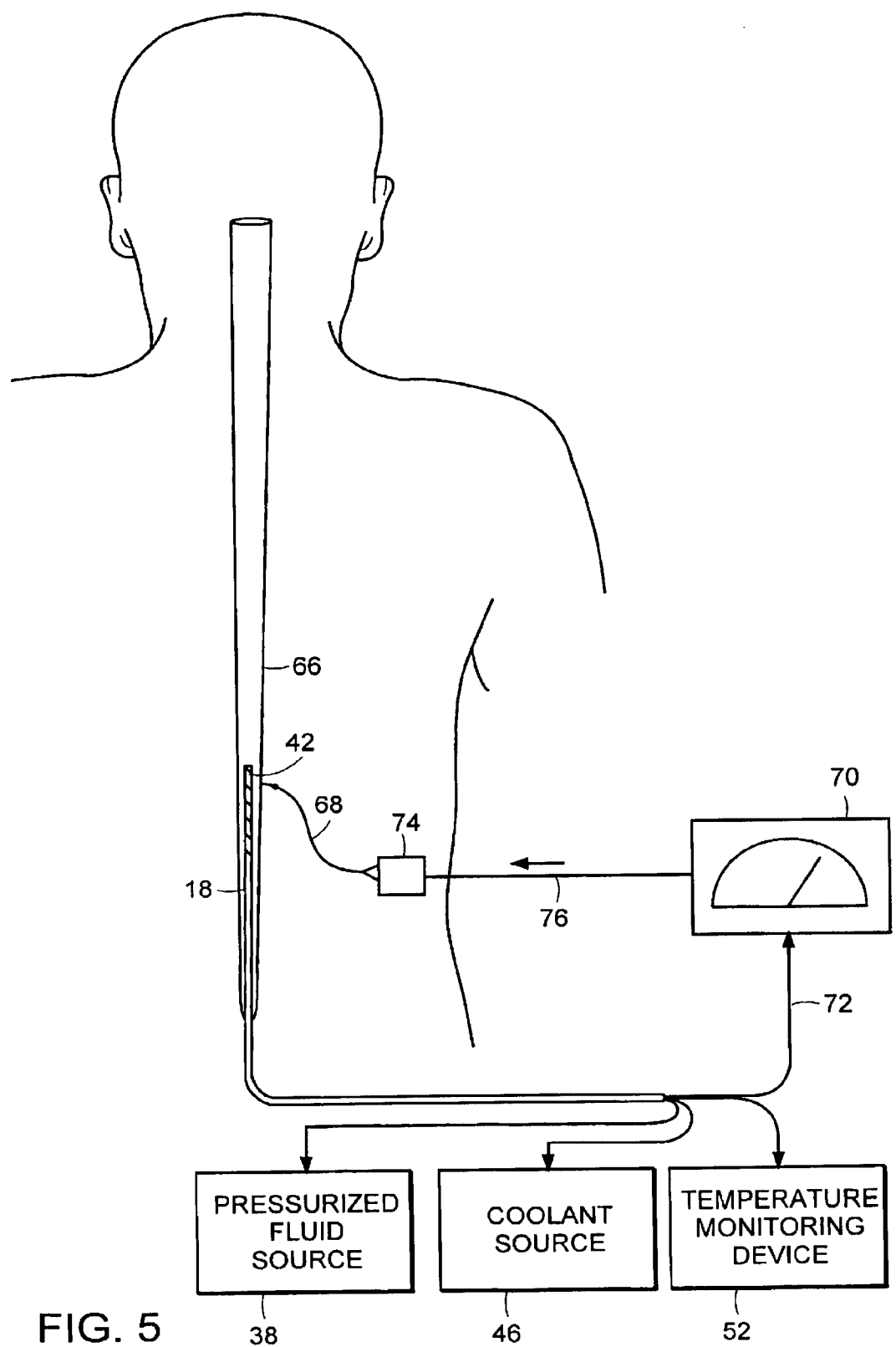
FIG. 5 is a schematic view of a circuit for measuring sensory evoked potentials in a patient.

The electrodiagnostic methods of the present invention are illustrated in FIG. 5, which schematically shows the cryocatheter 18 positioned in a patient's neuroaxis 66. A monitoring/stimulating device 70 is electrically connected to the tip member 42 (functioning as an electrode) via a first electrical lead 72 that passes through the cryocatheter 18. An external electrode 74 is applied to the exterior of the patient's body, on the dermatome that corresponds to the desired neuronal target site in the neuroaxis. The external electrode 74 is electrically connected to the monitoring/stimulating device 70 via a second electrical lead 76. The monitoring/stimulating device 70 is capable of generating an electrical stimulus for stimulating nerve endings of a dermatome. The monitoring/stimulating device 70 is also capable of receiving signals from the tip member 42 and measuring and displaying evoked potentials in response to such signals. Many devices for measuring and displaying evoked potentials are commercially available. The monitoring/stimulating device 70 can be any device suitable for such use, including commercially available devices, except that the device 70 will be used with the tip member 42 as the detecting electrode instead of a conventional scalp electrode.

When the tip member 42 is believed to be located at the desired target site in the neuroaxis, a measured electrical stimulus is applied to the corresponding dermatome via the external electrode 74. This electrical stimulus will be conducted centrally by the corresponding sensory (afferent) nerve 68, including the target neuronal tissue, to the spinal cord. If the tip member 42 is in contact with the appropriate target neuronal tissue, an electrical circuit will be completed. That is, the electrical stimulus will be conducted from the monitoring/stimulating device 70 to the external electrode 74 via the second electrical lead 76, from the external electrode 74 to the tip member 42 via the sensory (afferent) nerve 68, and from the tip member 42 to the monitoring/stimulating device 70 via the first electrical lead 72. The monitoring/stimulating device 70 thus provides detection of the dermatomal sensory evoked potential when the tip member 42 is properly located. The design of the cryocatheter 18, which provides for direct contact of the tip member 42 with the target neuronal tissue (as opposed to an electrode on the patient's scalp), greatly enhances the magnitude, sensitivity and specificity of the dermatomal sensory evoked potential.

When the device 70 detects a sensory evoked potential, this serves as an indication that the tip member 42 is properly positioned. At this point, the cooling/freezing treatment of the target site can be carried out. As the target neuronal tissue is cooled, nerve conduction will be interrupted (before freezing) and thereby eliminate or reduce pain. Moreover, nerve conduction interruption will also result in cessation of the sensory evoked potential. Thus, induced functional impairment of the target neuronal tissue will be confirmed when the device 70 ceases to measure a sensory evoked potential. This further verifies that the tip member 42 has been properly positioned and means that protracted cooling or freezing can be carried out to complete the procedure.

As mentioned above, the neuro-cryocatheter system provides cryoanalgesia by cooling or freezing of neuroaxis structure targets. Cooling mixed nerves produces a nerve conduction block wherein motor function is affected before sensory function. Selection of sensory, dorsal nerve structures as targets for cooling/freezing will render this irrelevant. The motor function is in the ventral nerve root, separated from the dorsal root by the denticulate ligament. Large myelinated sensory (afferent) fibers are affected and cease conduction before unmyelinated fibers. Small diameter myelinated fibers appear to be the most sensitive to cold. The most common neuronal tissue associated with pain is a small diameter unmyelinated fiber in the dorsal root.

When cooling neuronal tissue, the nerve conduction block is complete above 0 degrees centigrade, but prolonged conduction disturbances occur only by achieving temperatures of −5 to −20 degrees centigrade. At temperatures between −5 and −20 degrees centigrade neuropraxis may occur without neuronal destruction. Freezing generally occurs at temperatures below −20 degrees centigrade. Once freezing has occurred, no benefit is obtained by achieving by lower temperatures. There is little inflammatory response to freezing and if tissue structures (for example, the endoneurium) are not disrupted, nerve regeneration is possible. Recovery from freezing is accomplished in cases where axon destruction is followed by axonal regeneration. This process of regeneration has been studied and reported in medical literature.

In operation, cryocatheter 18 is introduced into the subarachnoid space of the spinal canal (dorsal aspect) by percutaneous spinal canal puncture. Specifically, after skin preparation, the introducer 10 is inserted into the subarachnoid space at the desired location, and the stylet 12 is removed, leaving the sheath 14 in place to function as a cannula. The structure of the meninges is such that the subarachnoid space can be entered posteriorly, by percutaneous puncture between the spinous processes. The distal end 22 of the cryocatheter 18 is inserted through the sheath 14 and into the subarachnoid space on the dorsal side of the spinal cord. The cryocatheter 18 is oriented such that the expandable portion 37 faces the dorsal dura mater and the tip member 42 faces the dorsal side of the spinal cord.

The distal end 22, and hence the tip member 42, are advanced to the target neuronal tissue. Proper positioning of the distal end 22 can be accomplished with imaging guidance. For instance, providing the cryocatheter 18 with a radio-opaqueness allows the distal end 22 to be placed adjacent to the target neuronal tissue with the aid of radiological imaging. The cryocatheter 18 could also be made of non-magnetic (non-polarizable) material for use in an open MRI device. The external electrode 74 is placed on the patient's body, on the dermatome that corresponds to the target neuronal tissue, and the device 70 is turned on such that the electrodiagnostic function of the cryocatheter 18 is operating.

There are many possible neuroaxis structure targets that could be selected for cooling or freezing with cryocatheter 18. Referring to FIG. 6, which is a dorsal view of a portion of a spinal cord 78 with the arachnoid mater 80 and the dura mater 82 shown pulled back, and FIG. 7, which is a composite diagram of a spinal cord segment and its corresponding dermatome, the basic structure of the neuroaxis and its possible targets will be described. The spinal cord 78 is comprised of the interior gray matter 84 and the white matter 86, which encompasses the gray matter 84. The gray matter 84 includes two ventral horns 88 and two dorsal horns 90. The arachnoid mater 80 completely surrounds the spinal cord 78, and the dura mater 82 surrounds the arachnoid mater 80. The subarachnoid space 91, several millimeters in depth and filled with spinal fluid, lies between the spinal cord 78 and the arachnoid mater 80. There are 30 paired spinal nerves 92 emanating from the spinal cord (8 cervical, 12 thoracic, 5 lumbar, 5 sacral), three of which are shown in FIG. 6 and one in FIG. 7 (shown extending through a vertebrae 93). Each spinal nerve 92 is divided into dorsal root filaments 94 and ventral root filaments 96 within the subarachnoid space 91. The dorsal root filaments 94, which are composed of sensory nerve fibers, enter the dorsal horn 90 of the spinal cord 78. The ventral root filaments 96, which are composed of motor nerve elements, emanate from the ventral horn 88. The anatomic separation is accentuated by the denticulate ligament 98, which lies between the dorsal root filaments 94 and the ventral root filaments 96. The nerve root filaments are made up of nerve axons. The nerve root filaments 94 and 96 are represented by single axons in FIG. 7. Dorsal axons extend to the dermatome 99 that corresponds to the respective spinal cord segment, as shown in FIG. 7. Ventral axons extend to a corresponding muscle (not shown). The dorsal root ganglia 100 (represented by a single nerve cell body in FIG. 7), which lie lateral of the dorsal root filaments 94 in the subarachnoid space 91, contain the neuronal bodies of most of the afferent nerve axons. With the exception of the head, the dorsal root filaments 94 of the paired spinal nerves 92 supply the major sensory input of the body.

Accordingly, the dorsal root filaments 94 are a primary target for cooling or freezing. Because these are sensory nerve structures, interrupting conduction by cooling or freezing will reduce or eliminate pain that would otherwise be transmitted by the nerve structures. The ventral root elements 96 (which are separated from the dorsal root elements by the denticulate ligament) are concerned with motor function and generally are not targets for the relief of pain. Other possible targets include the dorsal root ganglia 100, which contain the neuronal cell bodies of the dorsal root elements, and the dorsal horn 90 (particularly Rexed levels 1–4, or even Rexed levels 1–5). Lissauer's tract, which is adjacent to the dorsal horn 90, is also a potential target for cooling or freezing.

Visceral afferent nerve fibers conducting pain signals also enter the spinal cord via the dorsal roots. By rendering the dorsal root neuronal elements or the dorsal horn non-functional (non-conductive) along the cord at various levels both visceral and peripheral nerve sensory afferents can be controlled. It should therefore be possible to alleviate pain in viscera by cooling or freezing the appropriate spinal targets. For example, pancreatic pain could be alleviated this way.

Figure 8:
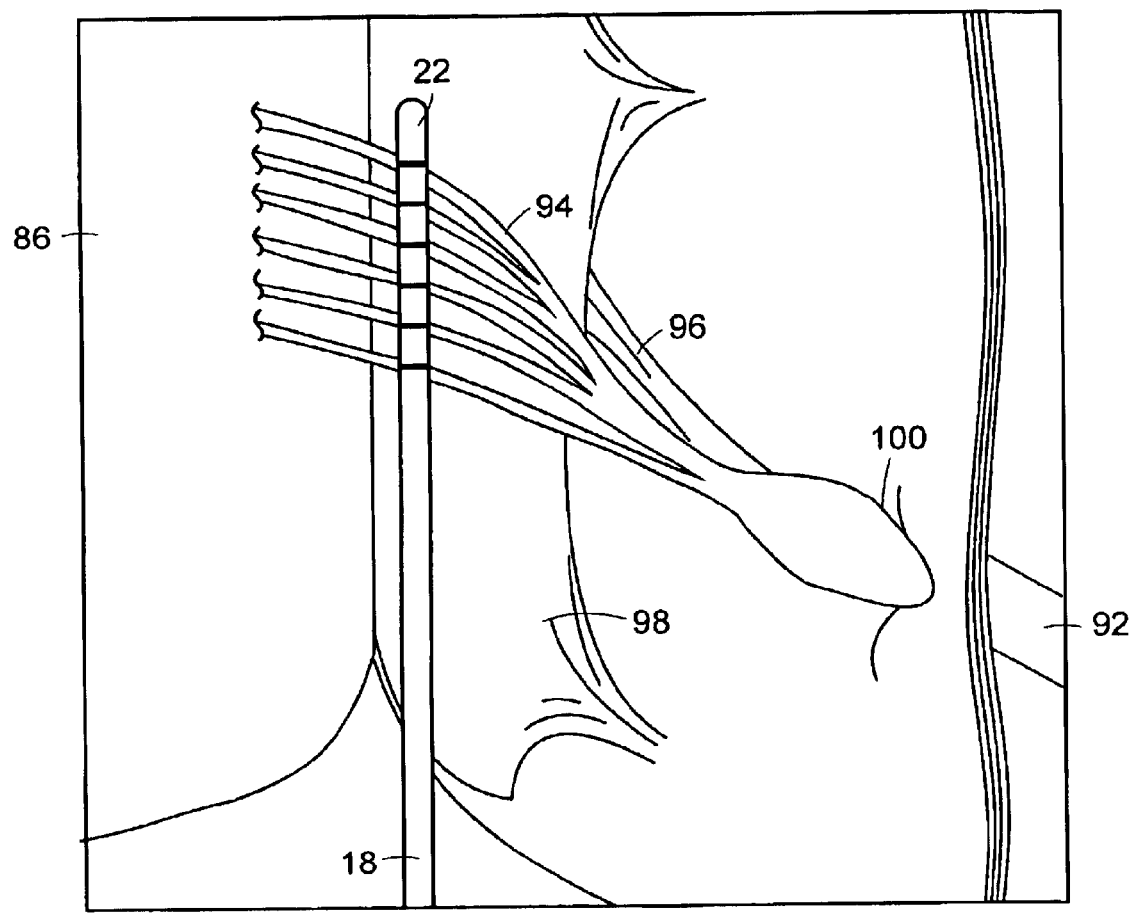
FIG. 8 is an enlarged dorsal view of the spinal cord of FIG. 6 showing the distal end of a cryocatheter located adjacent to a set of dorsal root filaments.

As mentioned above, the distal end 22 of the cryocatheter 18 is inserted into the subarachnoid space and advanced until the tip member 42 is adjacent to the target neuronal tissue. For example, the distal end 22 is schematically shown as being adjacent to a set of dorsal root filaments 94 in FIG. 6. FIG. 8 shows the location of the distal end 22 relative to the dorsal root filaments 94 in more detail. With the tip member 42 believed to be properly positioned adjacent to the target tissue, the dorsal expandable portion 37 of the cryocatheter 18 is inflated with pressurized fluid from the source 38, as controlled by the valve 40, until it expands into contact with the arachnoid mater 80 and the adjacent dura mater 82 and presses the tip member 42 on the ventral surface of the cryocatheter 18 into contact with the dorsal neuronal target. Thus, inflation of the expandable portion 37 holds the distal end 22 in position relative to the target neuronal tissue. As discussed above, reception of dermatomal sensory evoked potentials by the device 70 indicates that the tip member 42 is properly positioned.

Once the tip member 42 is fixed in the proper position, the valve 48 is opened to admit a flow of coolant fluid to the coolant delivery tube 44. The coolant fluid exits the tube 44 via the opening(s) 45, expands, and thereby cools the tip member 42. The temperature of the tip member 42 is monitored by the temperature detector 50. By monitoring the tip member temperature, the operator will be able to control the flow of coolant fluid so as to gradually cool the tip member 42, and hence the neuronal target tissue. Functional impairment of the target neuronal tissue induced by cooling or freezing will be confirmed by cessation of the dermatomal evoked sensory potential measured by the device 70.

Depending on the goals of the procedure, the neuronal tissue will be cooled or frozen. If cooled, the procedure may be carried out for extended periods of time. If neuronal tissue is frozen, continued application of the freezing process beyond that necessary to achieve at least −20 degrees centigrade is unnecessary.

If the cryocatheter 18 is being used for diagnostic purposes only (i.e., being used to determine the functional status of neuronal tissue), the procedure is the same as that described above except that the cooling/freezing steps are omitted and the diagnostic information would be obtained by measuring dermatomal sensory evoked potentials off the neuronal tissue while stimulating the appropriate dermatome. For example, the use of this function could maintain spinal cord function during neurosurgery.

The affect of cooling or freezing of neuroaxis tissue will be impacted by the particular anatomic site chosen (the target neuronal tissue), the rate of cooling or freezing, the temperature achieved, the duration of cooling in some circumstances, and thawing/freezing cycles, if employed. (Thawing/freezing cycles refers to small ice crystals thawing and the water being subsequently refrozen by larger ice crystals.) Freezing results in the withdrawing of water from biologic systems and the deposition of water in ice crystals. The development of ice crystals depends upon a) crystal nucleation rate and b) the ice crystal growth rate. Both of these factors are dependent on temperature and the rate of cooling. These factors are also tissue type specific and may not be linear with fall in temperature. The location of the ice crystals (i.e., intracellular versus extracellular) is dependent on the rate of cooling, with rapid freezing promoting the formation of intracellular ice crystals and increasing the risk of ultimate cell death. The size of the crystals for a given amount of water (in tissue) is a function of the number of crystals initiated by the process. The rate of temperature fall may well be a dominant variable. This in turn will be a function of efficiency by which a system removes heat. Anatomic considerations, such as blood vessel supply (blood flow) and cerebrospinal flow rates, may well impact the cooling rate. Recrystallization (i.e., the growth of large crystals at the expense of smaller ones) will influence the final nature and the extent of tissue damage and may occur during thawing. Thawing/freezing cycles, if employed, will impact the final lesion.

When the rate of cooling is slow, ice crystal nucleation occurs in the extracellular space drawing water out of the cell. The result is a formation of a few large, generally extracellular, crystals. The further result is such as to leave the cell membrane largely intact; membrane rupture is uncommon. This is useful when freezing nerve axons, leaving the endoneurium intact which allows for axonal regeneration. Extracellular ice crystal formation is unlikely to cause cell death even if the cell body is cooled or frozen. Freezing of vascular tissue that results in ischemia of the end-organ tissue may also be a factor in the destruction of the cell within the ice ball. However, the vascular supply of the spinal cord appears diffuse with multiple collaterals such that ischemia may not be a problem.

The geometry of the tip member 42 is a factor in lesion production since the tissue immediately adjacent to the tip member 42 will freeze more quickly and thoroughly. Moreover, the size of the ice ball, a field of cooling gradients, is correlated to the tip geometry. This could result in intracellular ice near the tip member 42 and extracellular ice away from the tip member 42. In any event, it is anticipated that there will be a freezing gradient related to the tip member 42 and its configuration.

Neuronal cell death (as opposed to axonal disruption) is likely to occur when a critical temperature achieved. This is believed to be −4 degrees centigrade or below and certainly is reached at −20 degrees centigrade. This temperature may be somewhat tissue dependent (for example, red blood cell versus neuronal tissue). There are reports of neuronal recovery for temperatures as low as −15 degrees centigrade. However, there appears to be a consensus that cells do not survive at temperatures lower than −20 degrees centigrade. Neuronal generation and conduction of nerve electropotentials ceases during cooling, but before nerve tissue is frozen. In addition, the electrical impedance of the tip member 42 goes up as ice is formed on it. Controlled cooling of the tip member 42 and the target tissue can avoid this and allow sensory evoked potential measurement.

An up to two hour exposure of neuronal tissue to cold temperature (e.g., between +5 and −5 degrees centigrade) will cool but not freeze the tissue and produce transient interruption of nerve conduction lasting hours or even days. When a mixed nerve is cooled, motor function is affected before sensory function. However, as previously noted, cooling the dorsal root or horn and the posterior cord itself should impact sensory function alone and not motor function. When neuronal cell bodies are frozen to −20 degrees centigrade or below, the duration of freezing becomes irrelevant because of the likelihood of cell death occurring.

If axons or nerve bodies are cooled, the return of function will return relatively quickly (i.e., over the course of many hours to several days). If axons are frozen, return of function will take many days or weeks as degeneration/regeneration of axons occur (axonal tissue regenerates at approximately 1–3 millimeters per day). If nerve bodies are frozen, neuronal function will generally not return. Accordingly, the target tissue should be selected carefully.

An alternative embodiment to the neuro-cryocatheter system described above would be to provide the cryogenic, electrodiagnostic, and pharmaceutical delivery functions with two or more catheters rather than a single catheter. Such an alternative system would include an introducer the same as or similar to the introducer 10 of FIG. 1 and a plurality of catheters. For instance, there could be a cryocatheter having cryogenic capabilities for cooling or freezing of neuroaxis structure targets and a separate catheter for delivering pharmaceuticals. There could also be another catheter having an electrode like the tip member 42 but no cryogenic capability. Such a catheter would be used for diagnostic purposes only (i.e., for determining the functional status of neuronal tissue).

While specific embodiments of the present invention have been described, it will be apparent to those skilled in the art that various modifications thereto can be made without departing from the spirit and scope of the invention as defined in the appended claims.

What is claimed is:

1. A method of freezing neuroaxis structure targets with a cryocatheter having a distal end and a proximate end, said method comprising:

inserting said distal end of said cryocatheter into the subarachnoid space of a patient; and delivering a coolant fluid into said cryocatheter so as to effect freezing of a neuronal tissue target.

2. The method of claim 1 further comprising positioning said distal end adjacent to said neuronal tissue target and wherein said coolant fluid is delivered to said distal end such that the temperature of said distal end is reduced.

3. The method of claim 2 further comprising using imaging guidance when positioning said distal end.

4. The method of claim 2 further comprising expanding at least a portion of said cryocatheter once said distal end is positioned adjacent to said neuronal tissue target.

5. The method of claim 2 further comprising measuring the temperature of said distal end and controlling delivery of said coolant fluid in response to distal end temperature.

6. The method of claim 2 further comprising applying an electrical stimulus to a dermatome on said patient that corresponds to said neuronal tissue target and using an electrode disposed on said cryocatheter to measure resultant sensory evoked potentials.

7. The method of claim 6 wherein measurement of sensory evoked potentials is used to verify that said distal end is properly positioned relative to said neuronal tissue target.

8. The method of claim 1 wherein said neuronal tissue target is selected from the group consisting of dorsal root filaments, dorsal root ganglia, dorsal horns, and Lissauer's tract.

9. A method of cooling or freezing neuroaxis structure targets with a cryocatheter having a distal end and a proximate end, said method comprising:
   inserting said distal end of said cryocatheter into the subarachnoid space of a patient;
   placing said distal end in contact with selected dorsal root filaments of said patient; and
   delivering a coolant fluid into said cryocatheter so as to effect cooling or freezing of said selected dorsal root filaments.

10. The method of claim 9 wherein placing said distal end in contact with selected dorsal root filaments includes positioning said distal end adjacent to said selected dorsal root filaments and expanding at least a portion of said cryocatheter.

11. The method of claim 10 further comprising using imaging guidance when positioning said distal end.

12. The method of claim 9 further comprising measuring the temperature of said distal end and controlling delivery of said coolant fluid in response to distal end temperature.

13. The method of claim 9 further comprising applying an electrical stimulus to a dermatome on said patient that corresponds to said selected dorsal root filaments and using an electrode disposed on said cryocatheter to measure resultant sensory evoked potentials.

14. The method of claim 13 wherein measurement of sensory evoked potentials is used to verify that said distal end is properly positioned relative to said selected dorsal root filaments.

15. A method of providing pain relief comprising:
   providing a cryocatheter having an electrically conductive tip member and means for cooling said tip member;
   introducing said tip member into the subarachnoid space of a patient by percutaneous spinal canal puncture;
   placing said tip member in contact with selected dorsal root filaments of said patient;
   applying a repetitive electrical stimulus to a dermatome on said patient that corresponds to said selected dorsal root filaments;
   using said electrically conductive tip member as an electrode to measure sensory evoked potentials that may result from applying said electrical stimulus, wherein detection of sensory evoked potentials provides confirmation that said tip member is properly positioned in contact with said selected dorsal root filaments;
   operating said means for cooling to cool said selected dorsal root filaments without freezing said selected dorsal root filaments subsequent to confirming that said tip member is properly positioned in contact with said selected dorsal root filaments;
   continuing to use said electrically conductive tip member as an electrode to measure sensory evoked potentials that may result from applying said electrical stimulus, wherein cessation of detected sensory evoked potentials subsequent to cooling said selected dorsal root filaments provides further confirmation that said tip member is properly positioned in contact with said selected dorsal root filaments;
   operating said cryocatheter to freeze said selected dorsal root filaments subsequent to further confirming that said tip member is properly positioned in contact with said selected dorsal root filaments; and
   withdrawing said tip member from said subarachnoid space subsequent to freezing said selected dorsal root filaments.

16. The method of claim 15 wherein said cryocatheter includes an expandable portion and the step of placing said tip member in contact with selected dorsal root filaments of said patient comprises:
   positioning said tip member adjacent to said selected dorsal root filaments; and
   expanding said expandable portion once said tip member is positioned adjacent to said selected dorsal root filaments so that said tip member is pressed into contact with said selected dorsal root filaments.

17. The method of claim 16 further comprising using imaging guidance when positioning said tip member.

18. The method of claim 15 further comprising monitoring temperature of said tip member to control cooling and freezing of said selected dorsal root filaments.

* * * * *